(12) United States Patent
Dacquay et al.

(10) Patent No.: US 7,674,243 B2
(45) Date of Patent: Mar. 9, 2010

(54) OPHTHALMIC INJECTION DEVICE USING PIEZOELECTRIC ARRAY

(75) Inventors: Bruno Dacquay, Irvine, CA (US); Casey Lind, Irvine, CA (US); Mike Martin, Newport Beach, CA (US)

(73) Assignee: Alcon Inc., Hunenberg (CH)

( * ) Notice: Subject to any disclaimer, the term of this patent is extended or adjusted under 35 U.S.C. 154(b) by 211 days.

(21) Appl. No.: 11/751,981

(22) Filed: May 22, 2007

(65) Prior Publication Data
US 2007/0270748 A1 Nov. 22, 2007

Related U.S. Application Data

(63) Continuation-in-part of application No. 11/581,629, filed on Oct. 16, 2006, and a continuation-in-part of application No. 11/435,906, filed on May 17, 2006, now abandoned.

(51) Int. Cl.
*A61M 37/00* (2006.01)
(52) U.S. Cl. ...................................... 604/131
(58) Field of Classification Search .................. 604/131
See application file for complete search history.

(56) References Cited

U.S. PATENT DOCUMENTS

| | | |
|---|---|---|
| 1,252,614 A | 1/1918 | Pieper |
| 3,089,815 A | 5/1963 | Lieb et al. |
| 3,608,549 A | 9/1971 | Merrill |
| 3,892,537 A | 7/1975 | Gulati et al. |
| 3,982,537 A | 9/1976 | Bucalo |
| 4,007,742 A | 2/1977 | Banko |
| 4,030,499 A * | 6/1977 | Bucalo ........................ 604/506 |
| 4,054,138 A | 10/1977 | Bucalo |
| 4,122,850 A | 10/1978 | Bucalo |
| 4,184,510 A | 1/1980 | Murry et al. |
| 4,246,932 A | 1/1981 | Raines |

(Continued)

FOREIGN PATENT DOCUMENTS

EP    0348146 A1    12/1989

(Continued)

OTHER PUBLICATIONS

"Ultra™ 2800 Positive Displacement Dispenser"; 2004; EFD, Inc. Brochure XP 1104 vol. 11.10; 2 pages.

(Continued)

*Primary Examiner*—Nicholas D Lucchesi
*Assistant Examiner*—Jason Flick
(74) *Attorney, Agent, or Firm*—Kenneth D. Bassinger

(57) ABSTRACT

An ophthalmic injection device has a dispensing chamber, a storage chamber, a piezoelectric array, a needle fluidly coupled to the dispensing chamber, a power source for providing power to the piezoelectric array, and a controller for controlling the power source. A dispensing chamber housing has an inner surface and an outer surface. The inner surface defines a dispensing chamber for receiving a quantity of a substance. The storage chamber is located near the dispensing chamber housing. The piezoelectric array is located between the storage chamber and the dispensing chamber housing. A housing at least partially encloses the dispensing chamber housing, the storage chamber, the piezoelectric array, the power source, and the controller. The piezoelectric array is activated to pump the substance from the storage chamber to the dispensing chamber.

24 Claims, 8 Drawing Sheets

U.S. PATENT DOCUMENTS

| | | | |
|---|---|---|---|
| 4,265,618 A | 5/1981 | Herskovitz et al. | |
| 4,357,136 A | 11/1982 | Herskovitz et al. | |
| 4,392,827 A | 7/1983 | Martin | |
| 4,474,752 A | 10/1984 | Haslam et al. | |
| 4,484,915 A | 11/1984 | Tartaglia | |
| 4,582,488 A | 4/1986 | Newman | |
| 4,684,344 A | 8/1987 | Brockway et al. | |
| 4,704,088 A | 11/1987 | Newman | |
| 4,713,446 A | 12/1987 | DeVore et al. | |
| 4,795,423 A | 1/1989 | Osterholm | |
| 4,830,855 A | 5/1989 | Stewart | |
| 4,992,045 A | 2/1991 | Beisel | |
| 5,066,276 A | 11/1991 | Wang | |
| 5,120,307 A | 6/1992 | Wang | |
| 5,261,883 A * | 11/1993 | Hood et al. | 604/153 |
| 5,328,481 A | 7/1994 | Wang | |
| 5,336,175 A | 8/1994 | Mames | |
| 5,360,413 A | 11/1994 | Leason et al. | |
| 5,370,630 A | 12/1994 | Smidebush et al. | |
| 5,476,511 A | 12/1995 | Gwon et al. | |
| 5,487,725 A | 1/1996 | Peyman | |
| 5,582,595 A | 12/1996 | Haber et al. | |
| 5,620,700 A | 4/1997 | Berggren et al. | |
| 5,743,886 A | 4/1998 | Lynn et al. | |
| 5,773,019 A | 6/1998 | Ashton et al. | |
| 5,783,205 A | 7/1998 | Berggren et al. | |
| 5,824,072 A | 10/1998 | Wong | |
| 5,860,949 A | 1/1999 | Chen | |
| 5,928,663 A | 7/1999 | Peyman | |
| 5,984,889 A | 11/1999 | Christ et al. | |
| 6,210,357 B1 | 4/2001 | Morris | |
| 6,270,343 B1 | 8/2001 | Martin | |
| 6,290,690 B1 | 9/2001 | Huculak et al. | |
| 6,364,865 B1 | 4/2002 | Lavi et al. | |
| 6,372,245 B1 | 4/2002 | Bowman et al. | |
| 6,413,245 B1 | 7/2002 | Yaacobi et al. | |
| 6,419,656 B1 | 7/2002 | Vetter et al. | |
| 6,436,143 B1 | 8/2002 | Ross et al. | |
| 6,488,659 B1 | 12/2002 | Rosenman | |
| 6,520,930 B2 | 2/2003 | Critchlow et al. | |
| 6,585,700 B1 | 7/2003 | Trocki et al. | |
| 6,589,229 B1 * | 7/2003 | Connelly et al. | 604/890.1 |
| 6,595,979 B1 | 7/2003 | Epstein et al. | |
| 6,635,267 B1 | 10/2003 | Miyoshi et al. | |
| 6,645,179 B1 | 11/2003 | Ishikawa et al. | |
| 6,726,654 B2 | 4/2004 | Rosenman | |
| 6,940,209 B2 | 9/2005 | Henderson | |
| 6,991,457 B2 | 1/2006 | Kazen et al. | |
| 7,176,030 B2 | 2/2007 | Faries, Jr. et al. | |
| 2002/0055720 A1 | 5/2002 | Hohlfelder et al. | |
| 2003/0055380 A1 | 3/2003 | Flaherty | |
| 2003/0125665 A1 | 7/2003 | Rosenman | |
| 2004/0039253 A1 | 2/2004 | Peyman et al. | |
| 2004/0052761 A1 | 3/2004 | Vernon et al. | |
| 2004/0133155 A1 | 7/2004 | Varner et al. | |
| 2004/0176720 A1 | 9/2004 | Kipfer | |
| 2004/0210200 A1 | 10/2004 | Gerondale et al. | |
| 2004/0231667 A1 * | 11/2004 | Horton et al. | 128/202.13 |
| 2005/0065477 A1 | 3/2005 | Jost | |
| 2005/0177137 A1 | 8/2005 | Kipfer | |
| 2006/0047250 A1 | 3/2006 | Hickingbotham | |

FOREIGN PATENT DOCUMENTS

| | | |
|---|---|---|
| EP | 0398394 | 11/1990 |
| GB | 1551767 | 8/1979 |
| WO | WO 82/03761 A1 | 11/1982 |
| WO | WO 87/00029 A1 | 1/1987 |
| WO | WO 96/03978 A1 | 2/1996 |
| WO | WO 99/33853 A2 | 7/1999 |
| WO | WO 01/10482 A1 | 2/2001 |
| WO | WO 2006/050008 A1 | 5/2006 |

OTHER PUBLICATIONS

"Parker: Your Resource for Motion and Fluid Control Components, Systems and Solutions—System Solutions for Life Sciences"; 2003; Aurora Instruments, LLC Brochure; 8 pages.

U.S. Appl. No. 11/200,452, filed Aug. 9, 2005, Hopkins.
U.S. Appl. No. 11/435,906, filed May 17, 2005, Dacquay, et al.
U.S. Appl. No. 11/486,870, filed Jul. 14, 2006, Marsh, et al.

* cited by examiner

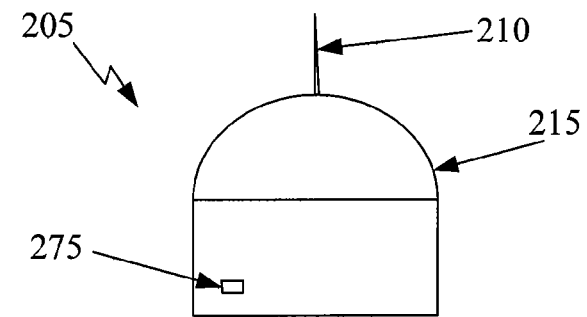
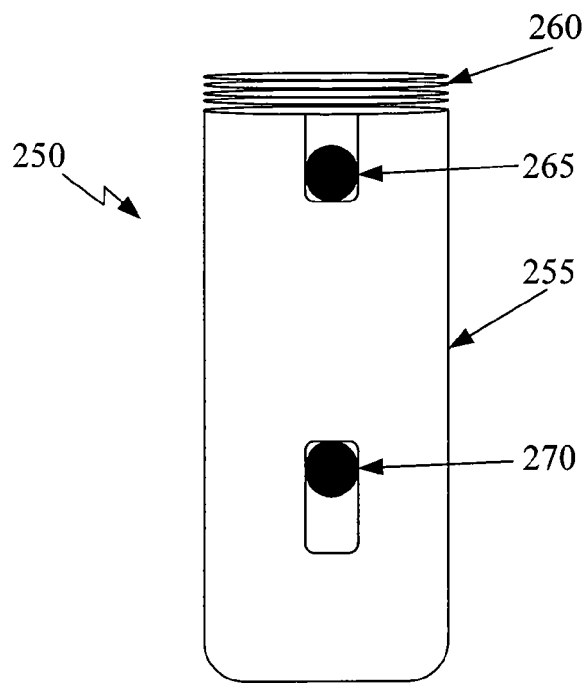
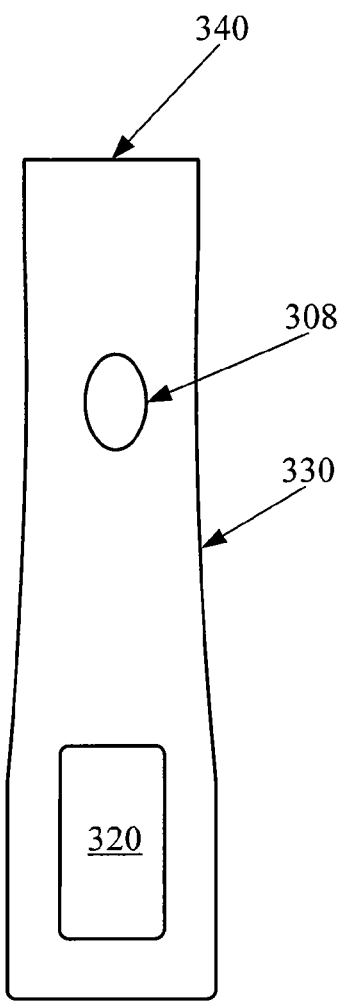
Fig. 2
Fig. 3

US 7,674,243 B2

OPHTHALMIC INJECTION DEVICE USING PIEZOELECTRIC ARRAY

RELATED APPLICATIONS

This Application is a continuation-in-part of U.S. patent application Ser. No. 11/581,629 filed Oct. 16, 2006 and U.S. patent application Ser. No. 11/435,906 filed May 17, 2006 now abandoned.

BACKGROUND OF THE INVENTION

The present invention relates to a medical device and more particularly to an ophthalmic drug delivery device containing piezoelectric array.

Several diseases and conditions of the posterior segment of the eye threaten vision. Age related macular degeneration (ARMD), choroidal neovascularization (CNV), retinopathies (e.g., diabetic retinopathy, vitreoretinopathy), retinitis (e.g., cytomegalovirus (CMV) retinitis), uveitis, macular edema, glaucoma, and neuropathies are several examples.

These, and other diseases, can be treated by injecting a drug into the eye. Such injections are typically manually made using a conventional syringe and needle. FIG. 1 is a perspective view of a prior art syringe used to inject drugs into the eye. In FIG. 1, the syringe includes a needle 105, a luer hub 110, a chamber 115, a plunger 120, a plunger shaft 125, and a thumb rest 130. As is commonly known, the drug to be injected is located in chamber 115. Pushing on the thumb rest 130 causes the plunger 120 to expel the drug through needle 105.

In using such a syringe, the surgeon is required to puncture the eye tissue with the needle, hold the syringe steady, and actuate the syringe plunger (with or without the help of a nurse) to inject the fluid into the eye. The volume injected is typically not controlled in an accurate manner because the vernier on the syringe is not precise relative to the small injection volume. Fluid flow rates are uncontrolled. Reading the vernier is also subject to parallax error. Tissue damage may occur due to an "unsteady" injection. Reflux of the drug may also occur when the needle is removed from the eye.

An effort has been made to control the delivery of small amounts of liquids. A commercially available fluid dispenser is the ULTRA™ positive displacement dispenser available from EFD Inc. of Providence, R.I. The ULTRA dispenser is typically used in the dispensing of small volumes of industrial adhesives. It utilizes a conventional syringe and a custom dispensing tip. The syringe plunger is actuated using an electrical stepper motor and an actuating fluid. Parker Hannifin Corporation of Cleveland, Ohio distributes a small volume liquid dispenser for drug discovery applications made by Aurora Instruments LLC of San Diego, Calif. The Parker/Aurora dispenser utilizes a piezo-electric dispensing mechanism. Ypsomed, Inc. of Switzerland produces a line of injection pens and automated injectors primarily for the self-injection of insulin or hormones by a patient. This product line includes simple disposable pens and electronically-controlled motorized injectors.

U.S. Pat. No. 6,290,690 discloses an ophthalmic system for injecting a viscous fluid (e.g. silicone oil) into the eye while simultaneously aspirating a second viscous fluid (e.g. perflourocarbon liquid) from the eye in a fluid/fluid exchange during surgery to repair a retinal detachment or tear. The system includes a conventional syringe with a plunger. One end of the syringe is fluidly coupled to a source of pneumatic pressure that provides a constant pneumatic pressure to actuate the plunger. The other end of the syringe is fluidly coupled to an infusion cannula via tubing to deliver the viscous fluid to be injected.

It would be desirable to have a portable hand piece for injecting a drug into the eye that includes reliable, low-cost technology. Piezoelectric actuators provide a technology that can be adapted for such use. It would be desirable to utilize piezoelectric actuators to dispense a drug. Such a system provides numerous benefits over prior art injectors.

SUMMARY OF THE INVENTION

In one embodiment consistent with the principles of the present invention, the present invention is an ophthalmic injection system having a tip segment attachable to and removable from limited reuse assembly. The tip segment includes a dispensing chamber, a storage chamber, a piezoelectric array, a needle fluidly coupled to the dispensing chamber, and a first housing at least partially enclosing the dispensing chamber housing, the storage chamber, and the piezoelectric array. A dispensing chamber housing has an inner surface and an outer surface. The inner surface defines a dispensing chamber for receiving a quantity of a substance. The storage chamber is located near the dispensing chamber housing. The piezoelectric array is located between the storage chamber and the dispensing chamber housing. The limited reuse assembly includes a power source for providing power to the piezoelectric array, a controller for controlling the power source, and a second housing at least partially enclosing the power source and the controller. The piezoelectric array is activated to pump the substance from the storage chamber to the dispensing chamber.

In another embodiment consistent with the principles of the present invention, the present invention is an ophthalmic injection device having a dispensing chamber, a storage chamber, a piezoelectric array, a needle fluidly coupled to the dispensing chamber, a power source for providing power to the piezoelectric array, and a controller for controlling the power source. A dispensing chamber housing has an inner surface and an outer surface. The inner surface defines a dispensing chamber for receiving a quantity of a substance. The storage chamber is located near the dispensing chamber housing. The piezoelectric array is located between the storage chamber and the dispensing chamber housing. A housing at least partially encloses the dispensing chamber housing, the storage chamber, the piezoelectric array, the power source, and the controller. The piezoelectric array is activated to pump the substance from the storage chamber to the dispensing chamber.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 2 is one view of an ophthalmic medical device including a disposable tip segment and a limited reuse assembly according to an embodiment of the present invention.

FIG. 3 is another embodiment of a limited reuse assembly according to the principles of the present invention.

DETAILED DESCRIPTION OF THE PREFERRED EMBODIMENTS

Figure 1:
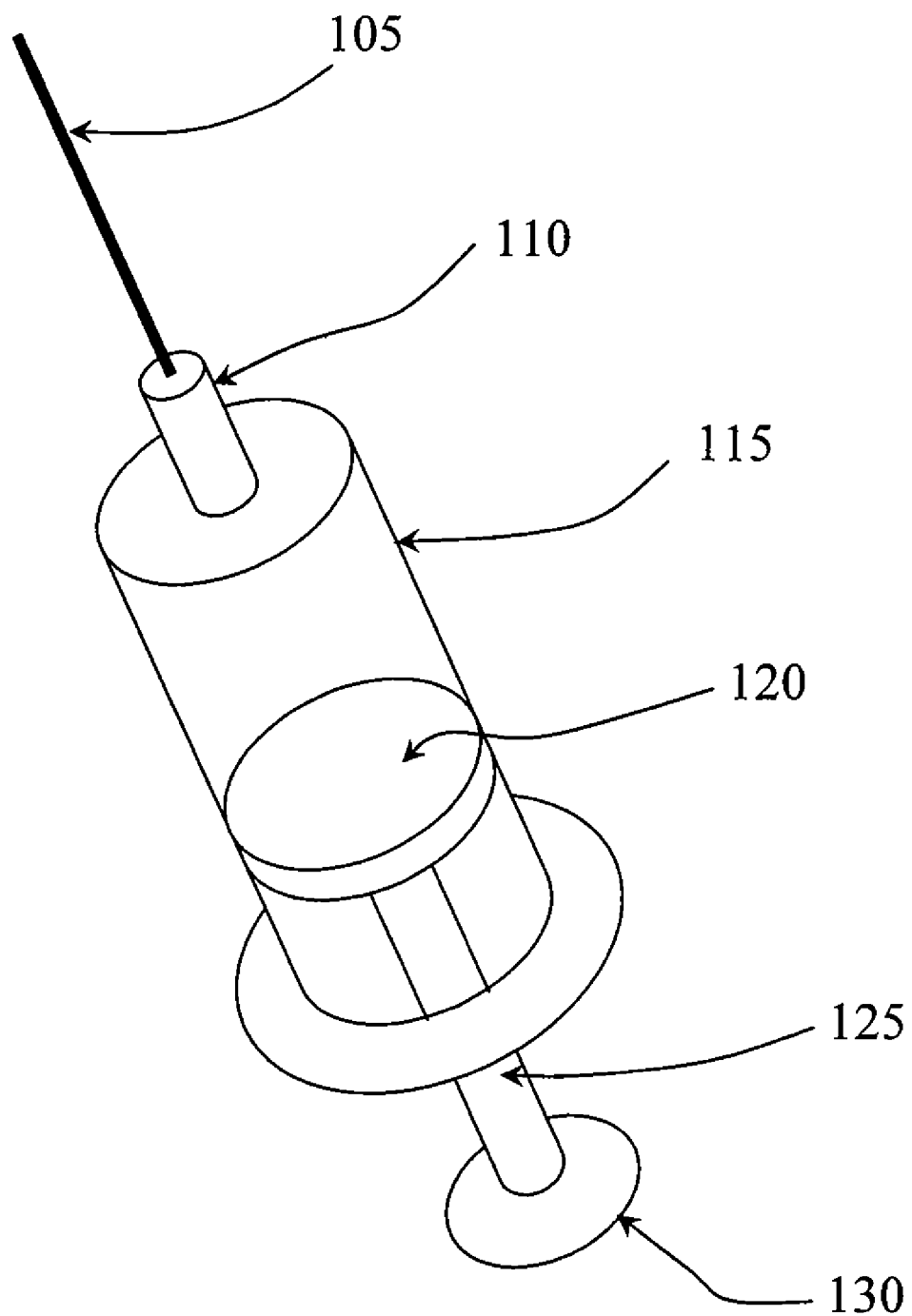
FIG. 1 is a perspective view of a prior art syringe.

Reference is now made in detail to the exemplary embodiments of the invention, examples of which are illustrated in the accompanying drawings. Wherever possible, the same reference numbers are used throughout the drawings to refer to the same or like parts.

FIG. 2 is one view of an ophthalmic medical device including a disposable tip segment and a limited reuse assembly according to an embodiment of the present invention. In FIG. 2, the medical device includes a tip segment 205 and a limited reuse assembly 250. The tip segment 205 includes a needle 210, a housing 215, and an optional light 275. The limited reuse assembly 250 includes a housing 255, a switch 270, a lock mechanism 265, and a threaded portion 260.

Tip segment 205 is capable of being connected to and removed from limited reuse assembly 250. In this embodiment, tip segment 205 has a threaded portion on an interior surface of housing 215 that screws onto the threaded portion 260 of limited reuse assembly 250. In addition, lock mechanism 265 secures tip segment 215 to limited reuse assembly 250. Lock mechanism 265 may be in the form of a button, a sliding switch, or a cantilevered mechanism. Other mechanisms for connecting tip segment 205 to limited reuse assembly 250, such as those involving structural features that mate with each other, are commonly known in the art and are within the scope of the present invention.

Needle 210 is adapted to deliver a substance, such as a drug, into an eye. Needle 210 may be of any commonly known configuration. Preferably, needle 210 is designed such that its thermal characteristics are conducive to the particular drug delivery application. For example, when a heated drug is to be delivered, needle 210 may be relatively short (several millimeters) in length to facilitate proper delivery of the drug.

Switch 270 is adapted to provide an input to the system. For example, switch 270 may be used to activate the system or to turn on a heater. Other switches, buttons, or user-directed control inputs are commonly known and may be employed with limited reuse assembly 250 and/or tip segment 205.

Optional light 275 is illuminated when tip segment 205 is ready to be used. Optional light 275 may protrude from housing 215, or it may be contained within housing 215, in which case, optional light 275 may be seen through a clear portion of housing 215. In other embodiments, optional light 275 may be replaced by an indicator, such as a liquid crystal display, segmented display, or other device that indicates a status or condition of disposable tip segment 205. For example, optional light 275 may also pulse on and off to indicate other states, such as, but not limited to a system error, fully charged battery, insufficiently charged battery or faulty connection between the tip segment 205 and limited use assembly 250. While shown on tip segment 205, optional light 275 or other indicator may be located on limited reuse assembly 250.

FIG. 3 is another embodiment of a limited reuse assembly according to the principles of the present invention. Limited reuse assembly 250 includes a button 308, a display 320, and a housing 330. Disposable tip segment 205 attaches to end 340 of limited reuse assembly 250. Button 308 is actuated to provide an input to the system. As with switch 270, button 308 may activate a heater or other temperature control device or initiate actuation of a plunger. Display 320 is a liquid crystal display, segmented display, or other device that indicates a status or condition of disposable tip segment 205 or limited reuse assembly 250.

Figure 4:
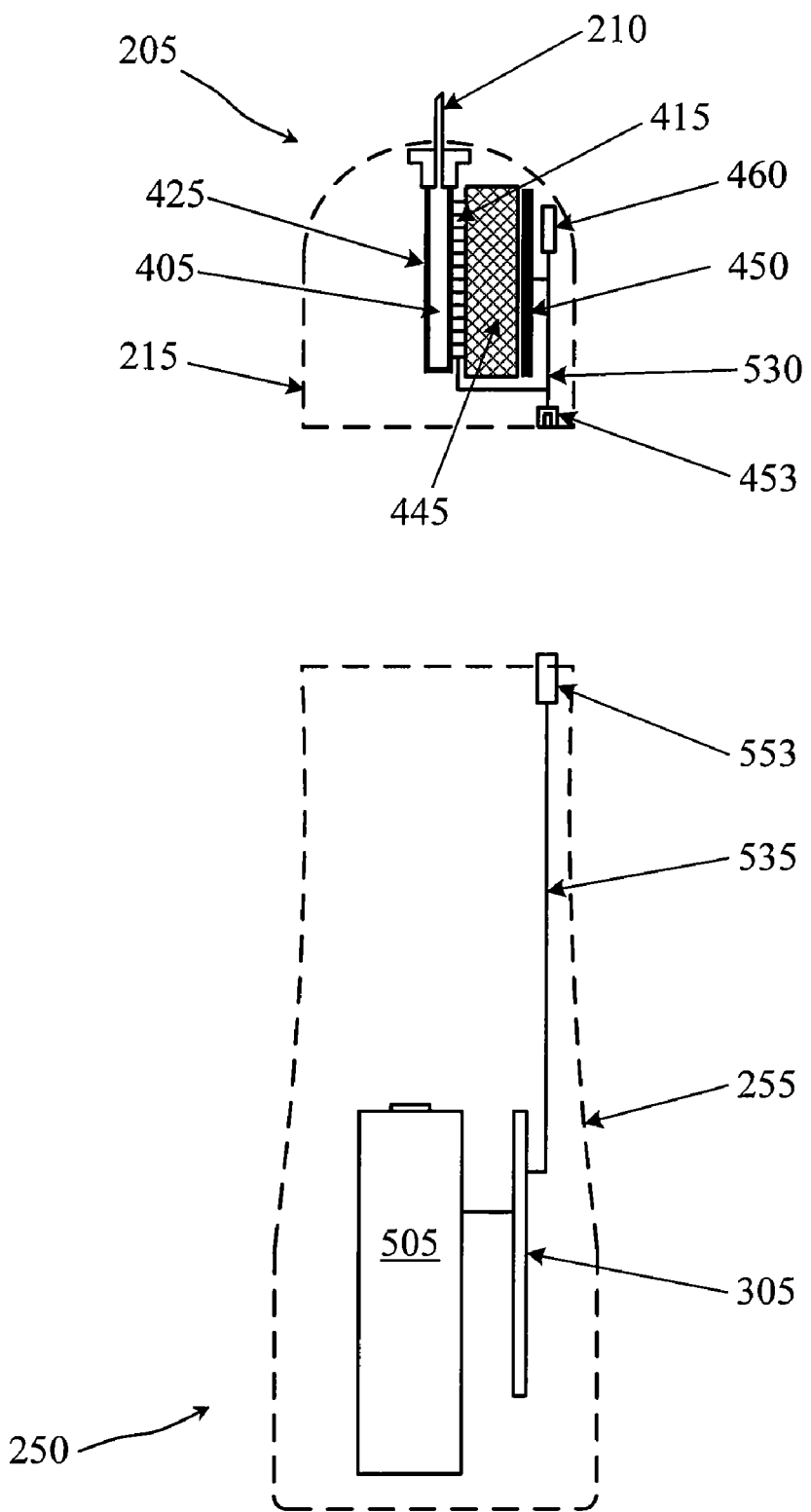
FIG. 4 is cross section view of a disposable tip segment and a limited reuse assembly according to an embodiment of the present invention.

FIG. 4 is cross section view of a disposable tip segment and a limited reuse assembly according to an embodiment of the present invention. FIG. 4 shows how tip segment 205 interfaces with limited reuse assembly 250. In the embodiment of FIG. 4, tip segment 205 includes dispensing chamber housing 425, dispensing chamber 405, storage chamber 445, optional heater 450, piezoelectric array 415, tip segment housing 215, thermal sensor 460, needle 210, interface 530, and tip interface connector 453. Limited reuse assembly 250 includes power source 505, controller 305, limited reuse assembly housing 255, interface 535, and limited reuse assembly interface connector 553.

In FIG. 4, dispensing chamber 405 is fluidly coupled to storage chamber 445 by piezoelectric array 415. When activated, piezoelectric array can pump a substance from storage chamber 445 to dispensing chamber 405. As such, dispensing chamber housing 425 has openings that interface with piezoelectric array 415. Optional heater 405 is located adjacent to or surrounds storage chamber 445. Thermal sensor 460 is located adjacent to heater 450 or storage chamber 445.

Piezoelectric array 415 is an array of piezoelectric actuators. The active element is basically a piece of polarized material (i.e. some parts of the molecule are positively charged, while other parts of the molecule are negatively charged) with electrodes attached to two of its opposite faces. When an electric field is applied across the material, the polarized molecules will align themselves with the electric field, resulting in induced dipoles within the molecular or crystal structure of the material. This alignment of molecules will cause the material to change dimensions. This phenomenon is known as electrostriction. In addition, a permanently-polarized material such as quartz (SiO2) or barium titanate (BaTiO3) will produce an electric field when the material changes dimensions as a result of an imposed mechanical force. This phenomenon is known as the piezoelectric effect.

Piezoelectric array 415 is configured so that its elements act to pump a substance from storage chamber 445 to dispensing chamber 405 in a manner similar to that used in inkjet printers. While shown as a single array, piezoelectric array 415 may be comprised of multiple arrays or elements. Typically, piezoelectric arrays are made using high volume silicon chip technology. As such, a commercially available chip may be employed as piezoelectric array 415.

In FIG. 4, dispensing chamber housing 425 is tubular or cylindrical in shape thus making dispensing chamber 405 a similar shape. Dispensing chamber housing has perforations or openings that interface with piezoelectric array 415. Dispensing chamber housing 425 may be heated by an optional heater (not shown). In one embodiment according to the principles of the present invention, heater 450 heats both dispensing chamber 405 and storage chamber 445.

Storage chamber 405 holds a substance, typically a drug, that is to be delivered into an eye. Storage chamber 445 may be of any suitable configuration. Optional heater 450 heats the substance in storage chamber 445.

Optional thermal sensor 460 provides temperature information to assist in controlling the operation of tip segment 205. Thermal sensor 460 may be located near or in thermal contact with storage chamber 445 or dispensing chamber housing 425 and measure a temperature near them. Thermal sensor 460 may be any of a number of different devices that can provide temperature information. For example, thermal sensor 460 may be a thermocouple or a resistive device whose resistance varies with temperature. Thermal sensor is also electrically coupled to interface 530 or other similar interface.

Needle 210 is fluidly coupled to dispensing chamber 405. As such, a substance contained in dispensing chamber 405 can pass through needle 210 and into an eye. Interface 530 connects piezoelectric array 415, optional heater 450, and optional thermal sensor 460 with tip interface connector 453.

In limited reuse assembly 250, power source 505 is typically a rechargeable battery, such as a lithium ion battery, although other types of batteries may be employed. In addition, any other type of power cell is appropriate for power source 505. Power source 505 provides current to dispensing chamber housing 425 to heat it and change its shape. Optionally, power source 505 can be removed from housing 255 through a door or other similar feature (not shown).

Controller 305 is typically an integrated circuit with power, input, and output pins capable of performing logic functions. In various embodiments, controller 305 is a targeted device controller. In such a case, controller 305 performs specific control functions targeted to a specific device or component, such as a temperature control device or a power supply. For example, a temperature control device controller has the basic functionality to control heater 450. In other embodiments, controller 305 is a microprocessor. In such a case, controller 305 is programmable so that it can function to control more than one component of the device. In other cases, controller 305 is not a programmable microprocessor, but instead is a special purpose controller configured to control different components that perform different functions. While depicted as one component in FIG. 4, controller 305 may be made of many different components or integrated circuits.

Controller 305 is connected via interface 535 to limited reuse assembly interface connecter 553. Limited reuse assembly interface connecter 553 is located on a top surface of limited reuse assembly housing 255. In this manner, limited reuse assembly interface connector 553 is adapted to be connected with tip interface connector 453 to provide an electrical connection between tip segment 205 and limited reuse assembly 250.

An interface between power source 505 and controller 305 allows controller 305 to control operation of power source 505. In such a case, controller 305 may control the charging and the discharging of power source 505 when power source 505 is a rechargeable battery.

In operation, when tip segment 205 is connected to limited reuse assembly 250, controller 305 controls the operation of piezoelectric array 415 and optional heater 450. Controller 305 directs power to actuate piezoelectric array 415 and heater 450. In one embodiment, a first current is directed to heater 450 to heat the substance in storage chamber 445. Once the substance has reached the proper temperature, the piezoelectric array is actuated so that the substance in storage chamber 445 is pumped into dispensing chamber 405 where it exits needle 210 and is injected into an eye.

A substance to be delivered into an eye, typically a drug suspended in a phase transition compound, is located in dispensing chamber 405. In this manner, the drug and phase transition compound are contained in storage chamber 445. The phase transition compound is in a solid or semi-solid state at lower temperatures and in a more liquid state at higher temperatures. Heater 450 can be activated to heat the compound to a more liquid state, piezoelectric array can be activated to inject the compound into the eye where it forms a bolus that erodes over time.

In one embodiment of the present invention, the substance located in storage chamber 445 is a drug that is preloaded into the dispensing chamber. In such a case, tip segment 205 is appropriate as a single use consumable product. Such a disposable product can be assembled at a factory with a dosage of a drug installed.

Figure 5A:
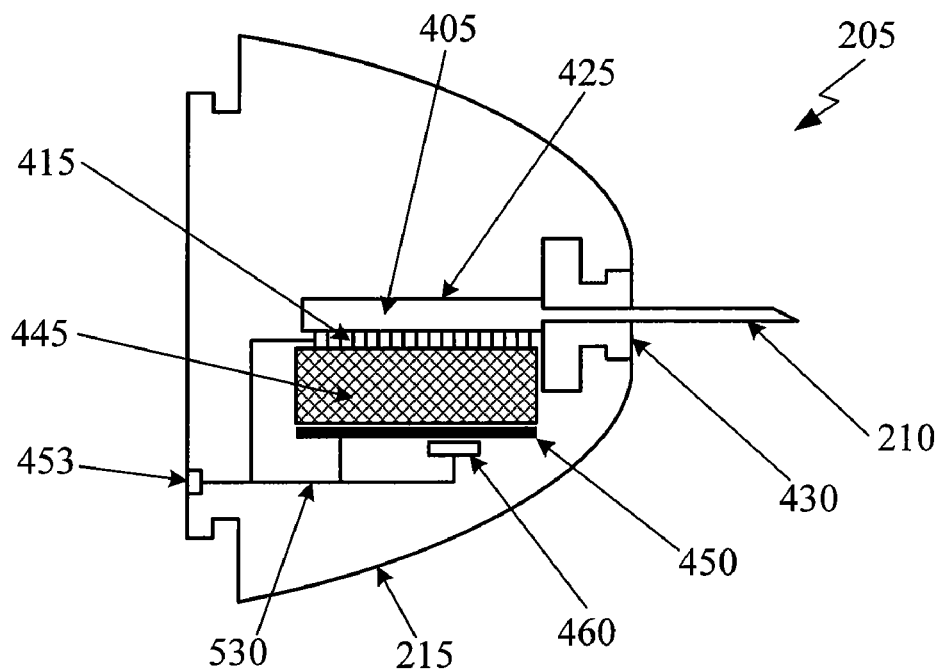
FIGS. 5A and 5B are exploded cross section views of disposable tip segments for an ophthalmic medical device according to an embodiment of the present invention.
Figure 5B:
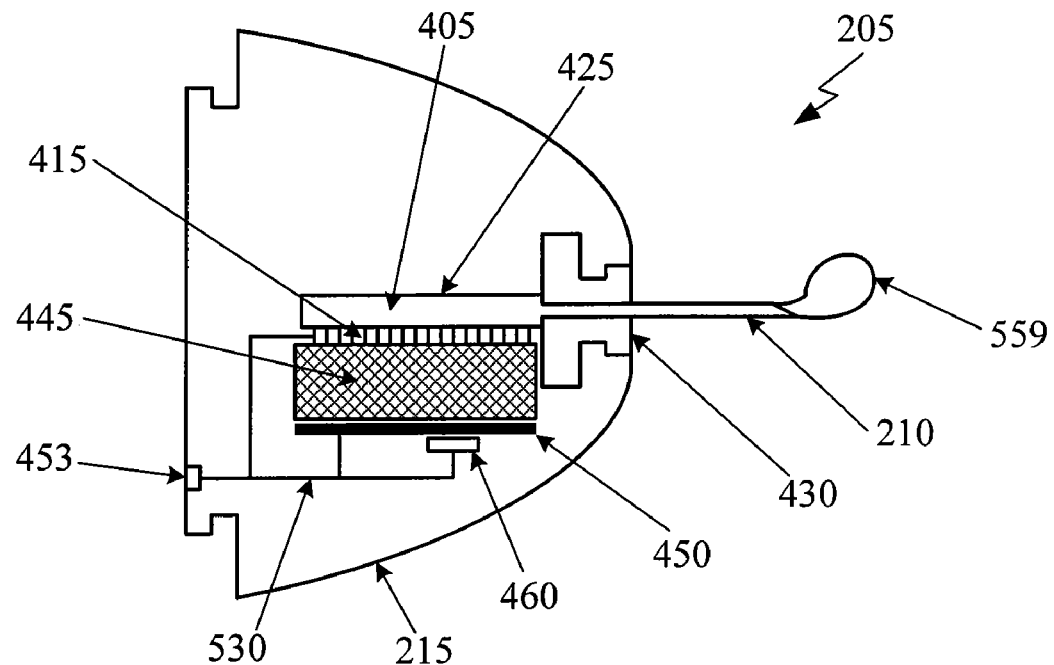

FIGS. 5A and 5B are exploded cross section views of disposable tip segments for an ophthalmic medical device according to an embodiment of the present invention. In FIG. 5A, piezoelectric array 415 has not been activated. In FIG. 5B, piezoelectric array 415 has been activated. In FIGS. 5A and 5B, an optional luer is also picture to secure needle 210.

In FIG. 5A, a current is applied to heater 450 to heat the substance in storage chamber 445. The current applied to the heater 450 can be regulated to control the temperature of the substance contained in storage chamber 445. For example, the amount of current (typically DC current) can be controlled to precisely control the temperature of heater 450. The more current applied to heater 450, the greater its temperature. Thermal sensor 460 provides temperature information to controller 305, so that it can control the amount of current sent to heater 450. Controller 305 may employ any of a number of different control algorithms, such as, for example, a PID algorithm.

After the substance has reached the proper temperature, piezoelectric array 415 can be activated to pump the substance from storage chamber 445 to dispensing chamber 405 as depicted in FIG. 5B. Piezoelectric array may be controlled to deliver a certain dosage and to deliver that dosage at a certain rate. The power applied to piezoelectric array 415 can be regulated to control a dosage and rate of delivery of the substance in dispensing chamber 405. As is known, a piezoelectric actuator, such as those in piezoelectric array 415, can be controlled very precisely and can make very precise movements. Such precise control can be applied to piezoelectric array 415 to precisely control the amount of substance transferred from storage chamber 445 to dispensing chamber 405 as well as the rate of that transfer.

Figure 6A:
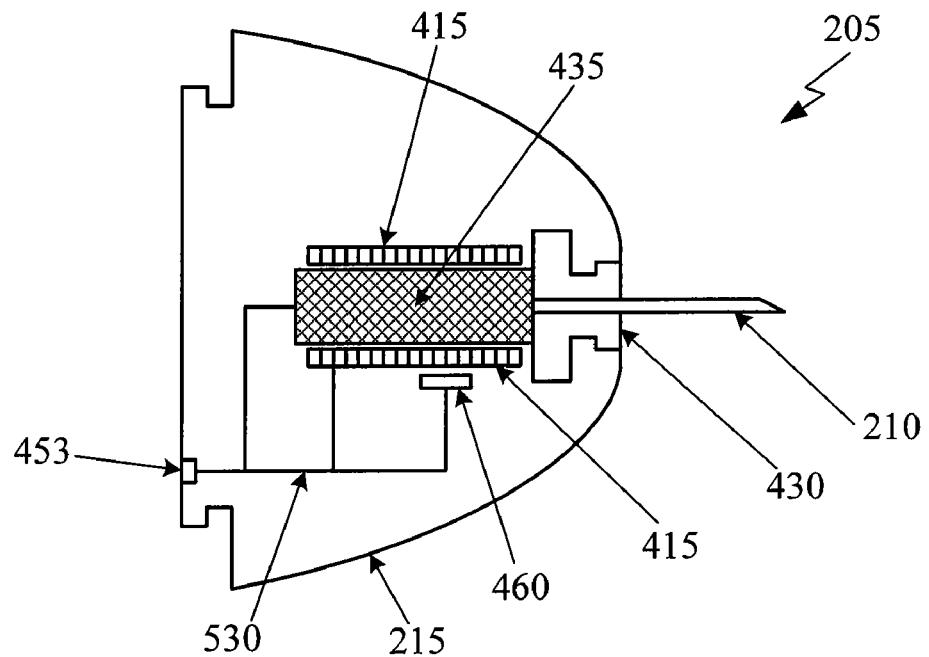
FIGS. 6A and 6B are exploded cross section views of disposable tip segments for an ophthalmic medical device according to an embodiment of the present invention.
Figure 6B:
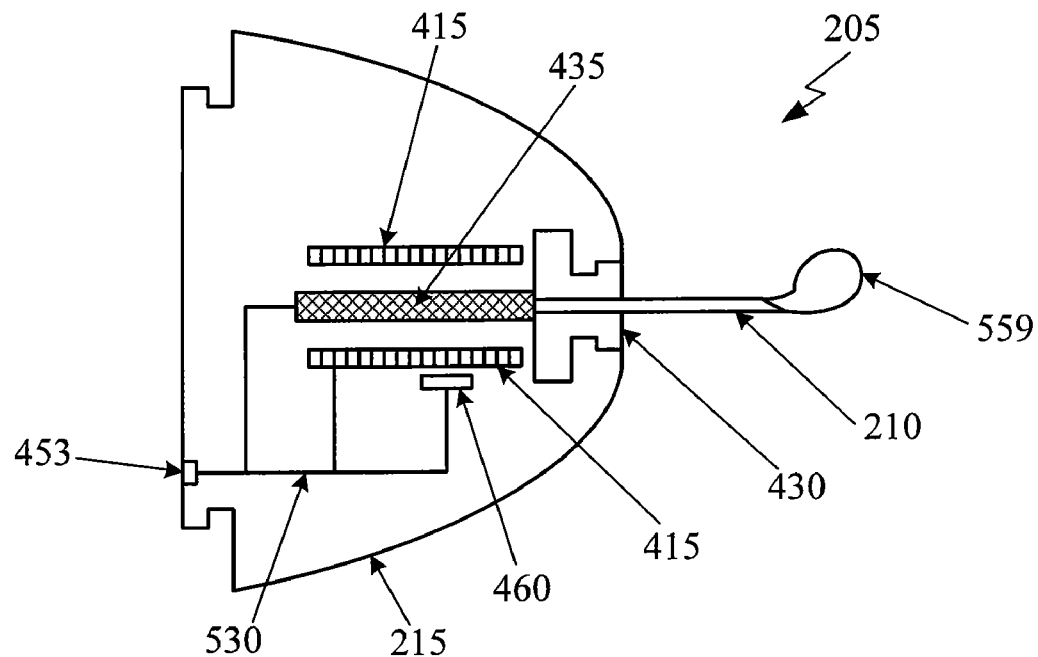

FIGS. 6A and 6B are exploded cross section views of disposable tip segments for an ophthalmic medical device according to an embodiment of the present invention. In FIG. 6A, piezoelectric array 415 has not been activated. In FIG. 6B, piezoelectric array 415 has been activated. In FIGS. 6A and 6B, a flexible chamber 435 is positioned between two piezoelectric arrays 415 as shown. In other embodiments, any number of piezoelectric arrays 415 may be positioned about flexible chamber 435. Needle 210 is fluidly coupled to flexible chamber 435. Thermal sensor 460 is located near flexible chamber 435. An optional luer is also picture to secure needle 210.

In FIGS. 6A and 6B, the piezoelectric arrays 415 are actuated to compress flexible chamber 435 and dispense a substance contained therein. Since the application of a voltage across a piezoelectric element causes that element to change shape (and expand when crystals align), piezoelectric arrays 415 can be activated to compress flexible chamber 435, decreasing its volume and expelling a substance from needle 210. This is shown in FIG. 6B in which the piezoelectric arrays 415 have been activated to compress flexible chamber 435 and expel substance 559. As with FIG. 5, piezoelectric array 415 can be precisely controlled to precisely control the amount of substance delivered and the rate at which that substance is delivered.

Flexible chamber 435 may also have a heater (not shown) disposed around it or in proximity to it. This heater (not shown) can function like the heater 450 of FIG. 5.

Figure 7:
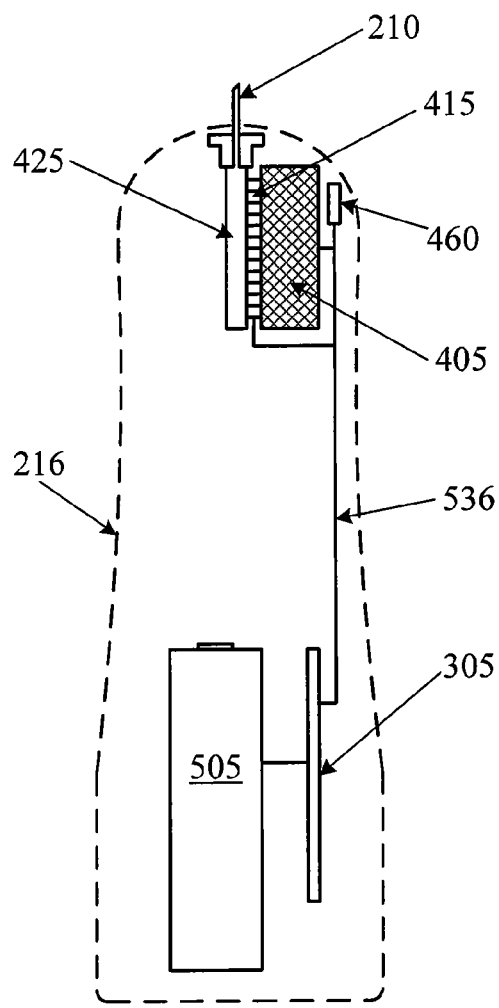
FIG. 7 is a cross section view of an ophthalmic injection device according to the principles of the present invention.
Figure 8:
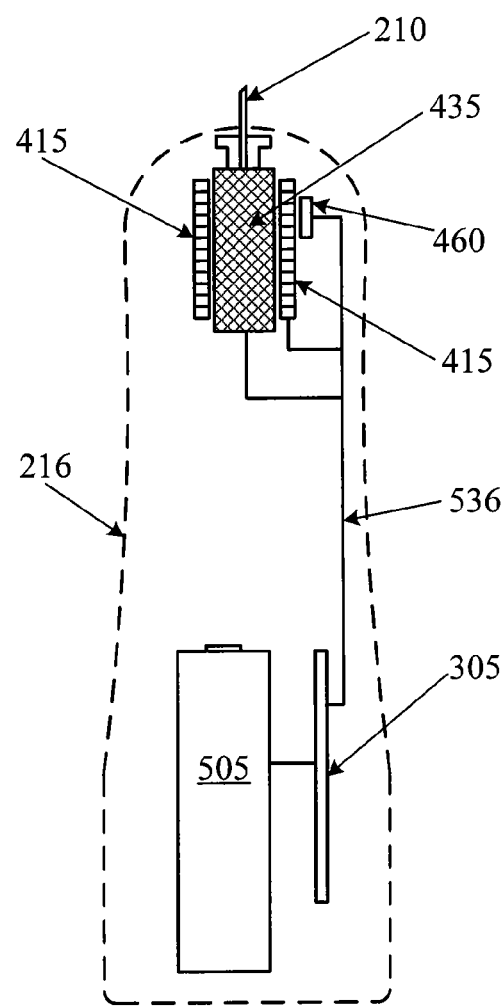
FIG. 8 is a cross section view of an ophthalmic injection device according to the principles of the present invention.

FIGS. 7 and 8 are cross section views of ophthalmic injection devices according to the principles of the present invention. In FIGS. 7 and 8, the injection device is integrated into a single unit. The single piece device of FIGS. 7 and 8 operates in the same manner as the two piece device previously described. In FIGS. 7 and 8, a single interface 536 is used instead of two separate interfaces (530 and 535) and two separate connectors (453 and 553). Housing 216 encloses the components pictured.

Figure 9:
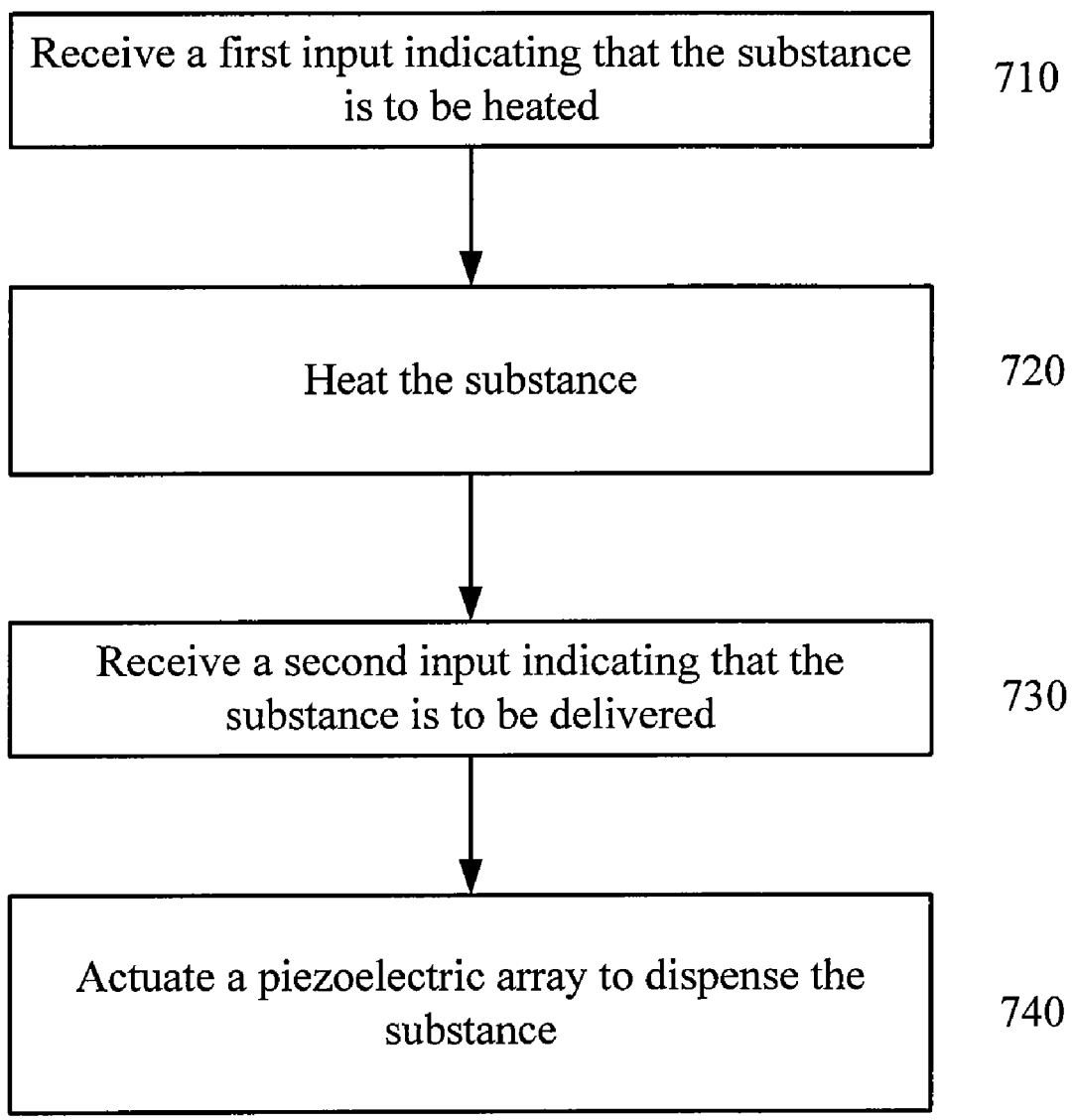
FIG. 9 is a flow chart of one method of delivering a substance into an eye using a shape memory alloy.

FIG. 9 is a method of delivering a substance into an eye using a piezoelectric array. In 710, a first input indicating that a substance is to be heated is received. In 720, the substance is heated. In 730, a second input is received indicating that the substance is to be delivered. In 740, after the substance is heated, a piezoelectric array is activated to dispense the substance.

Figure 10:
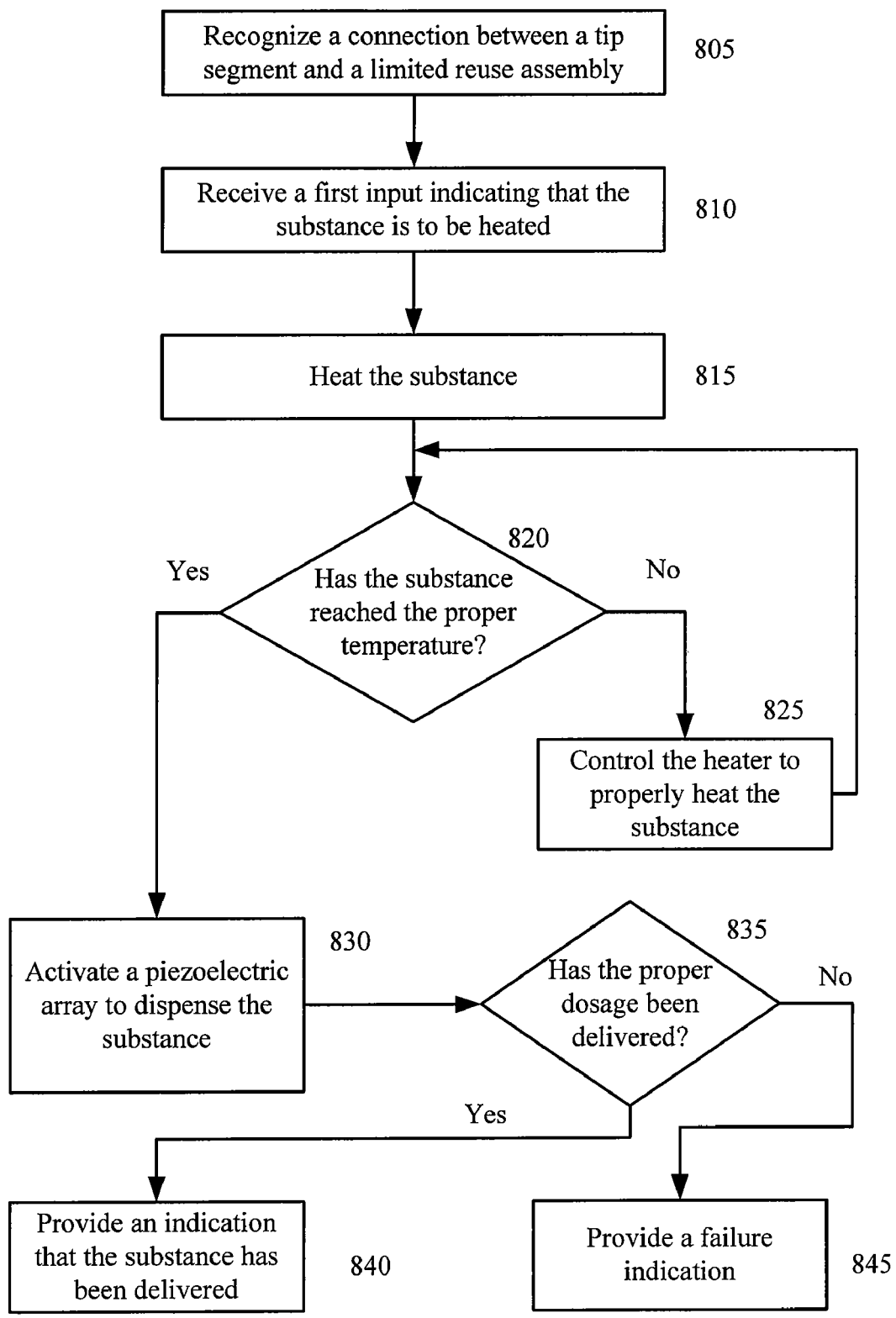
FIG. 10 is a flow chart of one method of delivering a substance into an eye using a shape memory alloy.

FIG. 10 is a method of delivering a substance into an eye using a piezoelectric array. In 805, a connection between a tip segment and a limited reuse assembly is recognized. In 810, a first input indicating that a substance is to be heated is received. In 815, the substance is heated. In 820, a determination is made as to whether the substance has reached the proper temperature. If the substance has not reached the proper temperature, then in 825 the heater is controlled to properly heat the substance. If the substance has reached the proper temperature, then in 830, a piezoelectric array is activated to deliver the substance. In 835, a determination is made as to whether the proper dosage has been delivered. If the proper dosage has been delivered, then in 840 an indication that the substance has been delivered is provided. If the proper dosage has not been delivered, then in 845 a failure indication is provided.

From the above, it may be appreciated that the present invention provides an improved system and methods for delivering precise volumes of a substance into an eye. The present invention provides a piezoelectric array that can dispense a substance. In one embodiment, a disposable tip segment that interfaces with a limited reuse assembly is employed. In another embodiment, a single unit is employed. The present invention is illustrated herein by example, and various modifications may be made by a person of ordinary skill in the art.

While the present invention is described in the context of a single-use drug delivery device, the present invention encompasses any injection device. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An injection system comprising:
    a tip segment attachable to and removable from a limited reuse assembly;
    the tip segment comprising:
        a dispensing chamber housing having an inner surface and an outer surface, the inner surface defining a dispensing chamber for receiving a quantity of a substance, the dispensing chamber housing having a plurality of perforations;
        a storage chamber located near the dispensing chamber housing;
        a piezoelectric array located between the storage chamber and the dispensing chamber housing, the piezoelectric array fluidly coupled to the plurality of perforations;
        a needle fluidly coupled to the dispensing chamber; and
        a first housing at least partially enclosing the dispensing chamber housing, the storage chamber, and the piezoelectric array;
    the limited reuse assembly comprising:
        a power source for providing power to the piezoelectric array;
        a controller for controlling the power source; and
        a second housing at least partially enclosing the power source and the controller;
    wherein the piezoelectric array is activated to pump the substance from the storage chamber, through the plurality of perforations, to the dispensing chamber.

2. The system of claim 1 wherein the tip segment further comprises:
    a heater for heating the substance.

3. The system of claim 2 wherein the tip segment further comprises:
    a thermal sensor located near the storage chamber, the thermal sensor for measuring a temperature.

4. The system of claim 3 further comprising:
    an interface connecting the thermal sensor to the controller.

5. The system of claim 4 wherein the controller uses the measured temperature to control the heater.

6. The system of claim 3 wherein the controller uses the measured temperature to control the piezoelectric array.

7. The system of claim 1 wherein the controller controls the piezoelectric array to control an amount of the substance that is delivered.

8. The system of claim 1 wherein the controller controls the piezoelectric array to control a rate at which the substance is delivered.

9. The system of claim 1 wherein the power source is a rechargeable battery.

10. The system of claim 1 wherein the tip segment further comprises:
    a tip interface connector located on an interfacing surface of the tip segment; and
    a limited reuse assembly interface connector located on an interfacing surface of the limited reuse assembly, the limited reuse assembly interface connector attachable to the tip segment interface connector.

11. The system of claim 1 wherein the tip segment further comprises:
    a luer for securing the needle to the dispensing chamber housing.

12. The system of claim 1 wherein the substance is a drug for treating a condition of the eye.

13. The system of claim 1 wherein the limited reuse assembly further comprises:
    an indicator located on the second housing, the indicator for providing information about a status of substance delivery.

14. An injection device comprising:
    a dispensing chamber housing having an inner surface and an outer surface, the inner surface defining a dispensing chamber for receiving a quantity of a substance, the dispensing chamber housing having a plurality of perforations;

a storage chamber located near the dispensing chamber housing;

a piezoelectric array located between the storage chamber and the dispensing chamber housing, the piezoelectric array fluidly coupled to the plurality of perforations;

a needle fluidly coupled to the dispensing chamber;

a power source for providing power to the piezoelectric array;

a controller for controlling the power source; and a housing at least partially enclosing the power source, the controller, the dispensing chamber housing, the storage chamber, and the piezoelectric array;

wherein the piezoelectric array is activated to pump the substance from the storage chamber, through the plurality of perforations, to the dispensing chamber.

15. The device of claim 14 further comprising:
a heater for heating the substance.

16. The device of claim 15 further comprising:
a thermal sensor located near the storage chamber, the thermal sensor for measuring a temperature.

17. The device of claim 16 further comprising:
an interface connecting the thermal sensor to the controller.

18. The device of claim 17 wherein the controller uses the measured temperature to control the heater.

19. The device of claim 16 wherein the controller uses the measured temperature to control the piezoelectric array.

20. The device of claim 14 wherein the controller controls the piezoelectric array to control an amount of the substance that is delivered.

21. The device of claim 14 wherein the controller controls the piezoelectric array to control a rate at which the substance is delivered.

22. The device of claim 14 wherein the power source is a rechargeable battery.

23. The device of claim 14 wherein the substance is a drug for treating a condition of the eye.

24. The device of claim 14 wherein the device further comprises:
an indicator located on the housing, the indicator for providing information about a status of substance delivery.

* * * * *